United States Patent
Rizzuto et al.

(10) Patent No.: US 9,724,284 B2
(45) Date of Patent: Aug. 8, 2017

(54) METHOD FOR REMOVING A TATTOO

(71) Applicant: CONAIR CORPORATION, Stamford, CT (US)

(72) Inventors: Leandro P. Rizzuto, Sheridan, WY (US); Lawrence Cruz, Weston, CT (US)

(73) Assignee: Conair Corporation, Stamford, CT (US)

( * ) Notice: Subject to any disclaimer, the term of this patent is extended or adjusted under 35 U.S.C. 154(b) by 0 days.

(21) Appl. No.: 14/740,643

(22) Filed: Jun. 16, 2015

(65) Prior Publication Data

US 2016/0367458 A1 Dec. 22, 2016

(51) Int. Cl.
*A61K 8/46* (2006.01)
*A61K 8/22* (2006.01)
*A61K 8/894* (2006.01)
*A61K 8/891* (2006.01)
*A61K 8/24* (2006.01)
*A61K 8/81* (2006.01)
*A61Q 1/14* (2006.01)

(52) U.S. Cl.
CPC .............. *A61K 8/46* (2013.01); *A61K 8/22* (2013.01); *A61K 8/24* (2013.01); *A61K 8/8141* (2013.01); *A61K 8/891* (2013.01); *A61K 8/894* (2013.01); *A61Q 1/145* (2013.01); *A61K 2800/30* (2013.01)

(58) Field of Classification Search
None
See application file for complete search history.

(56) References Cited

U.S. PATENT DOCUMENTS

| | | | | |
|---|---|---|---|---|
| 2,985,500 A | * | 5/1961 | Janson | D06P 5/138 252/188.2 |
| 2007/0166252 A1 | | 7/2007 | Hattendorf et al. | |
| 2014/0242012 A1 | * | 8/2014 | Cozzi | A61K 31/22 424/62 |

FOREIGN PATENT DOCUMENTS

GB 2465000 A 5/2010

OTHER PUBLICATIONS

Longhaircommnunity [retrieved from on-line website: http://forums.longhaircommunity.com/showthread.php?t=92419[Jan. 25, 2016].*
Obagi Nu-Derm Exfoderm Forte product ([retrieved from on-line website: http://www.dermstore.com/product_Nu-Derm+Exfoderm+Forte__1176.htm#collapseGlance, last visit Jan. 25, 2016]).*
Rongalite, Chemspider [retreived from on-line website: http://www.chemspider.com/Chemical-Structure.8649.html (last visit Jan. 27, 2016)].*
Hydrogen Peroixde [retrieved from on-line website: http://www.ibchem.com/faq/2008/08/14/why-can-hydrogen-peroxide-act-as-both-an-oxidising-agent-and-a-reducing-agent/, published in 2008, last access date: Jul. 10, 2016].*
Longhaircommnunity [retrieved from on-line website: http://forums.longhaircommunity.com/showthread.php?t=92419, published on Apr. 20, 2012, last access date Jul. 10, 2016].*
WD-40 ([retrieved from on-line website: https://en.wikipedia.org/wiki/WD-40, last visit Dec. 31, 2016]).*
International Cosmetic Ingredient Dictionary and Handbook, vol. 2, 1997, pp. 1-42.*
International Search Report dated Jul. 1, 2016 from corresponding International Application No. PCT/US2016/036005, 5 pages.
Written Opinion dated Jul. 1, 2016 from corresponding International Application No. PCT/US2016/036005, 7 pages.

* cited by examiner

Primary Examiner — Ernst V Arnold
Assistant Examiner — Kyung Sook Chang
(74) Attorney, Agent, or Firm — Ohlandt, Greeley, Ruggiero & Perle, L.L.P.

(57) ABSTRACT

A method of removing a tattoo from skin of a human subject. The method has the step of applying to a region of the skin having the tattoo a reducing composition that includes a reducing agent and a penetration enhancer in admixture. The penetration enhancer is present in an amount effective to effect penetration of at least at least a portion of the reducing agent through the skin to the location of the tattoo. The reducing agent is present in an amount effective to at least partially decolorize or break up a pigment of the tattoo. The reducing agent can be selected from the group consisting of sodium oxymethylene sulfoxylate and sodium hydroxymethane sulfinic acid.

17 Claims, No Drawings

METHOD FOR REMOVING A TATTOO

BACKGROUND OF THE DISCLOSURE

Field of the Disclosure

The present disclosure relates to a method for removing a tattoo. More particularly, the present disclosure relates to a method for removing a tattoo by administration of a topical composition to the skin having the tattoo.

Description of the Prior Art

Tattoos take the form of permanent marking and/or coloration of the skin. For a tattoo, permanent ink is applied to the dermis layer (underneath the epidermis or outer layer) of the skin via needle. A tattoo consists of thousands of particles of ink suspended in the skin. While normal human growth and healing processes will remove small foreign particles from the skin, tattoo ink particles are permanent because they are too large to be removed.

Removal of a tattoo from the skin can be painful, time-consuming, and difficult. Some techniques for removing tattoos include laser treatment, dermabrasion, surgical incision, and cryotherapy. Drawbacks to current removal techniques can, depending on technique, include change in skin pigmentation, scarring, pain and discomfort, multiple treatments, and cost. In many cases, full removal of a tattoo is never achieved because certain colors and types of ink are resistant to certain known techniques.

GB 2465000 discloses a method of removing a tattoo from a human subject. The method relates to application to the skin a composition having a peroxide and a transdermal carrier effective to carry the peroxide through the skin. The peroxide reacts with and decolorizes the pigments that make up the tattoo ink.

U.S. Patent Publication No. 2007/0166252 discloses a regimen for treating skin subject to tattoo removal procedures. The regimen has the sequential steps of applying a preparatory composition and a corrective composition to the skin. One embodiment of a corrective composition disclosed at [0043] of this patent publication has a skin lightening agent of hydroquinone, an emulsifier, an antioxidant, a reducing agent, and water (plus other ingredients).

It is desirable to have a method for removing tattoos that avoids such drawbacks as changing skin pigmentation, scarring, and pain and discomfort. It is also desirable to have a method for removing tattoos that is economical in cost and that has a higher success rate with a greater variety of ink colors and types. It is further desirable to have method for removing tattoos that can be carried out by a consumer.

SUMMARY OF THE DISCLOSURE

The present disclosure provides a method of removing a tattoo from the skin of a human subject that avoids the shortcomings described above and that effectively removes tattoos made from a wide variety of ink colors and types in an efficient, safe and comfortable manner.

The present disclosure further provides a method that has the step of applying to a region of the skin having the tattoo a reducing composition including a reducing agent and a penetration enhancer in admixture. The penetration enhancer is present in an amount effective to enhance the penetration of at least a portion of the reducing agent through the epidermis layer of the skin to reach the location of the tattoo in the dermis layer. The reducing agent is present in an amount effective to at least partially decolorize or break up a pigment of the tattoo.

DETAILED DESCRIPTION OF THE DISCLOSURE

The present disclosure provides a method of applying a reducing composition to a region of the surface of the skin overlaying the tattoo. The reducing composition is applied and allowed to penetrate the epidermis advance into the skin to diminish the intensity of the tattoo ink where it resides in the dermis. The reducing composition either decolorizes the pigments or chemically reduces pigments in the tattoo ink so that the size of pigment particles is reduced and, thus, allows the body to dissolve and/or carry off the smaller particles. The penetration or permeation of the reducing agent through the epidermis into the dermis (where the tattoo resides) is enhanced or facilitated by the presence of a penetration enhancer in the composition. The penetration enhancer increases the rate and level of penetration of the reducing agent compared to what it would be without the penetration enhancer. Optionally, after the reducing composition has been applied for a period of time, an oxidizing composition can be applied to surface of the skin overlaying the tattoo for the purpose of neutralizing and deactivating the reducing agent. Like the reducing composition, the oxidizing composition has a penetrating agent to enhance or facilitate the penetration of the oxidizing agent into the skin.

The reducing agent can take the form of any reducing agent known in the art used for topical or pharmaceutical application. Such reducing agents include those that reverse the oxidative coloring process of by decoupling of oxidative bonds. Preferred reducing agents include, but are not limited to, sodium oxymethylene sulfoxylate (sodium hydroxymethane sulfinic acid).

In the composition of the present disclosure, the amount and concentration of the reducing agent can vary depending on factors, such as properties and amounts of co-adjuvants and vehicles and the physical form of the composition. The amount of the reducing agent in the composition will be that effective to enhance the penetration of at least a portion of the reducing agent through the epidermis layer of the skin to reach the location of the tattoo residing in the dermis layer. The concentration of reducing agent in the composition will preferably be from about 1 wt % to about 80 wt %, more preferably from about 5 wt % to about 50 wt %, yet more preferably from about 10 wt % to about 40 wt %, most preferably from about 10 wt % to about 30 wt %, based on the total weight of the composition.

The reducing composition is topically administered to the surface of the skin (epidermis) overlaying the tattoo within the dermis. The reducing agent can penetrate or permeate through the epidermis and into the dermis, where the tattoo resides. The reducing composition can be applied once, or multiple times over a period of time, depending on the difficulty encountered in removing, i.e., dissolving or disintegrating the pigment particles of the tattoo ink, in the dermis. For instance, the reducing composition can be applied once (or more often) per day for one day or for multiple days in sequence.

Optionally, a second (oxidizing) composition having an oxidizing agent, such as inorganic peroxide, can be applied to the surface of the skin after the reducing composition has been left there for a period of time for the purpose of neutralizing or inactivating the reducing agent within and on the skin. Hydrogen peroxide is a preferred peroxide for use in the oxidizing composition.

The amount and concentration of the oxidizing agent in the oxidizing composition can vary depending on factors, such as properties and amount of co-adjuvants and vehicles and the physical form of the composition. The concentration of reducing agent in the present composition will be from about 1 wt % to about 80 wt %, preferably from about 5 wt % to about 50 wt %, more preferably from about 10 wt % to about 40 wt %, most preferably from about 10 wt % to about 30 wt %, based on the total weight of the composition. The oxidizing agent is typically provided in an aqueous form, particularly in the instance of peroxides.

Useful penetration enhancers for the reducing and the oxidizing agent include, but are not limited to, mineral oil, alcohols, polyol, fatty alcohol, fatty acid ester, surfactant, and emulsifier. Useful alcohols include $C_{2-6}$ alcohols, such as ethanol, propanol, isopropanol, and butanol. Useful polyols include ethylene glycol, propylene glycol, butylene glycol, and glycerin. Useful fatty alcohols include $C_{8-24}$ fatty alcohols, such as cetyl alcohol, cetostearyl alcohol, stearyl alcohol, lauryl alcohol, and behenyl alcohol (and ethoxylated derivatives thereof). Useful fatty esters include $C_{8-24}$ fatty esters, such as cetyl esters, cetostearyl esters, stearyl esters, lauryl esters, and behenyl esters (and ethoxylated derivatives thereof).

Solvents and vehicles/carriers, such as water, that do not impart substantial transdermal penetration to the agents may also be employed. Solvents and vehicles/carriers that do impart substantial transdermal penetration, such as ethanol and propylene glycol, to the agents may be employed as well. Penetration enhancers will typically be dissolved or dispersed within a solvent(s) or vehicle(s)/carrier(s).

Tattoo inks are colored pigments dissolved or suspended in a liquid or semisolid carrier. Examples of colored pigments that can be used in a tattoo ink include, but are not limited to, the following: iron oxide ($Fe_3O_4$ and $FeO$), carbon, logwood, ochres (iron oxides mixed with clay), napthol-AS pigment, disazodiarylide and/or disazopyrazolone, curcuma yellow, chromium oxide ($Cr_2O_3$) (casalis green or anadomis green), malachite [$Cu_2(CO_3)(OH)_2$], ferrocyanides and ferricyanides, lead chromate, monoazo pigment, Cu/Al phthalocyanine, Cu phthalocyanine, azure blue, cobalt blue, Cu-phthalocyanine, manganese violet (manganese ammonium pyrophosphate), aluminum salts, quinacridone, dioxazine/carbazole, lead white (lead carbonate), titanium dioxide ($TiO_2$), barium sulfate ($BaSO_4$), and zinc oxide. Suitable carriers for pigments include the carriers listed herein for the reducing agents and oxidizing agents but most typically are water, ethanol, methanol, denatured alcohols, propylene glycol, or glycerin.

The reducing composition of the present invention can effect partial or substantially complete removal of a tattoo. Thus, for example, the color intensity of the tattoo can be reduced by at least 10%, more typically at least 20%, preferably at least 30%, more preferably at least 50% and most preferably at least 75%. In particularly preferred embodiments of the present disclosure, the intensity of the tattoo can be reduced by 90% or more so that the tattoo is no longer visible. The color intensity of the tattoo can be determined by visual observation, colorimetry, or other known tests. The reduction in intensity can be achieved by a single application of the composition or collectively by multiple applications of the composition over time.

A thickener can be added to either the reducing composition or the oxidizing composition. A thickener provides a composition with physical consistency and viscosity that enable it to remain in place on the skin overlaying the tattoo. Examples of thickeners include, but are not limited to, silicas such as fumed silica; acrylate and methacrylate polymers and copolymers; cellulose polymers such as methylcellulose, hydroxymethylcellulose, hydroxyethylcellulose, and hydroxypropylmethylcellulose; and gums such as guar, carboxymethyl cellulose, carrageenan, gellan, xanthan, and locust bean.

Either the reducing composition or the oxidizing composition can optionally include one or more skin conditioning agents for the purpose of enhancing the emolliency and feel of the skin. For example, a composition can have one or more skin conditioning agents present in an amount up to 15%, and more preferably about 8 wt % to about 12 wt %, based on the total weight of the composition. If desired, it is possible to provide a skin conditioning composition as a standalone composition separate from either the reducing composition or the oxidizing composition.

Examples of useful skin conditioning agents include, but are not limited to, N-alkylcarboxylate-N-fatty alkyl-quaternary amines (betaines) and their corresponding ammonium compounds (zwitterionic compounds). Preferred skin conditioning agents include lauryl dimethyl amine glycinate, myristyl dimethyl amine glycinate, cetyl dimethyl amine glycinate, stearyl dimethyl amine glycinate, oleyl dimethyl amine glycinate, heptadecyl dimethyl amine glycinate, behenyl dimethyl amine glycinate, dimethyl cocamine glycinate, dimethyl hydrogenated tallow amine glycinate, bis (hydroxyethyl) cocamine glycinate, bis (hydroxyethyl) tallow amine glycinate, bis (hydroxypropyl) stearamine glycinate, bis (hydroxymethyl) behenamine glycinate, pentadecyl diethyl amine glycinate, tridecyl dipropyl amine glycinate, tridecyl bis (2-hydroxybutyl) amine glycinate, heptadecyl bis (2-hydroxybutyl) amine glycinate and tridecyloxypropyl bis (hydroxyethyl) amine glycinate. Another useful skin conditioning agent is allantoin.

Examples of useful emollients include, but are not limited to, monoglyceride esters, such as glyceryl stearate, and silicone oils, such a dimethicone, and plant-derived fats, such as Shea butter. Examples of useful humectants include, but are not limited to, glycerin, glycerol, and propylene glycol.

The reducing composition preferably has one or more preservatives. Such a preservative can be selected from, but are not limited to, alkyl parabens such as methyl parabens; ethyl parabens, propyl parabens and butyl parabens; imidazolinyl urea, and phenoxy ethanol. Useful preservatives include methylchloroisothiazolinone and methylisothiazolinone.

The reducing composition of present disclosure can, if desired, have one or more fragrances, such as, for example, hexyl cinnamaldehyde (hexyl cinamal), limonene, citronellol, *Calendula officinalis* (Marigold) extract and linalool.

The present composition can take any form known in the art as useful for topical application. Such forms include a cream, ointment, gel, lotion, poultice, paste, and patch. Cream and lotion are preferred forms. If desired, the cream or lotion can take the form of an emulsion, particularly an oil-in-water emulsion. The oily phase can include a hydrophobic component such as mineral oils or petrolatum.

Some penetration enhancers can provide additional functionality as emulsifiers when an emulsion form is desired. Such penetration enhancers include fatty acid esters of polyethylene glycol and fatty alcohols.

In one embodiment of the reducing composition, the composition is substantially free of hydroquinone, hydroquinone derivatives, or other whitening agents. The composition is further preferably substantially free of any reducing agents disclosed in the compositions in U.S. Patent Publication No. 2007/0166252, which is incorporated herein by reference in its entirety.

The following are examples of the present disclosure and are not to be construed as limiting.

EXAMPLES

Example 1 (Reducing Composition)

| Ingredient | Wt. % | Function |
|---|---|---|
| water (aqua) | 73.55% | solvent, carrier |
| sodium oxymethylene sulfoxylate | 20.00% | reducing agent |
| pentasodium pentetate | 2.00% | chelating agent |
| Ceteth-20 | 2.00% | solubilizer, carrier |
| hydroxyethylcellulose | 1.40% | thickening agent |
| fragrance (parfum) | 1.00% | fragrance |
| methylchloroisothiazolinone and methylisothiazolinone | 0.05% | preservative |

Example 2 (Oxidizing Composition)

The following oxidizing composition is topically applied to the skin after the reducing composition is similarly applied and allowed to penetrate into the skin to diminish the tattoo. The oxidizing composition neutralizes and deactivates the reducing composition. A penetration agent may optionally be added to the oxidizing composition to achieve a desired degree of penetration of the oxidizing agent

| Ingredient | Wt. % | Function |
|---|---|---|
| deionized water (aqua) | 90.372% | solvent, carrier |
| acrylates polymer | 5.00% | thickening agent |
| Hydrogen peroxide (50%) | 4.60% | oxidizing agent |
| dimethicone copolyol meadowfoamate | 0.01% | conditioner |
| simethicone | 0.01% | conditioner |
| Phosphoric acid | 0.008% | pH adjuster |

It should be understood that the foregoing description is only illustrative of the present disclosure. Various alternatives and modifications can be devised by those skilled in the art without departing from the present disclosure. Accordingly, the present disclosure is intended to embrace all such alternatives, modifications and variances which fall within the scope of the appended claims.

What is claimed is:

1. A method of removing a tattoo from skin of a human subject, consisting of the step of applying to a region of the skin having the tattoo a reducing composition, wherein the reducing composition includes a reducing agent and a first penetration enhancer in admixture in a first carrier that is different than the first penetration enhancer, wherein the first penetration enhancer is present in an amount sufficient to effect penetration of at least a portion of the reducing agent through the skin to the tattoo therein, wherein the reducing agent is present in an amount effective to at least partially decolorize or break up a pigment of the tattoo by chemically reducing the pigment so that the reducing composition effects chemical reduction of the pigment, and wherein the reducing agent is sodium oxymethylene sulfoxylate.

2. The method of claim 1, wherein the first penetration enhancer is selected from the group consisting of mineral oils, alcohols, polyols, fatty alcohols, and fatty acid esters.

3. The method of claim 1, wherein the reducing composition further includes a skin conditioning agent.

4. The method of claim 1, wherein the reducing composition is applied to the skin once per day.

5. The method of claim 1, wherein the reducing composition is applied to the skin multiple times per day.

6. The method of claim 1, wherein the reducing composition is applied to the skin once per day for multiple days in sequence.

7. A method of removing a tattoo from skin of a human subject, consisting of the steps of
   (a) applying to a region of the skin having the tattoo a reducing composition, wherein the reducing composition includes a reducing agent and a penetration enhancer in admixture, wherein the penetration enhancer is present in an amount effective to effect penetration of at least a portion of the reducing agent through the skin to the tattoo therein, and wherein the reducing agent is present in an amount sufficient to at least partially decolorize or break up a pigment of the tattoo and to chemically reduce the pigment, and wherein the reducing agent is sodium oxymethylene sulfoxylate so that the reducing composition effects chemical reduction of the pigment; and
   (b) applying, after a period of time, an oxidizing composition to the region of the skin having the tattoo.

8. The method of claim 7, wherein the oxidizing composition includes an oxidizing agent and a second penetration enhancer admixed in a second carrier.

9. The method of claim 8, wherein the second penetration enhancer is present in an amount effective to penetrate the oxidizing agent through the skin to the location of the tattoo, and wherein the oxidizing agent neutralizes any remaining reducing agent.

10. The method of claim 8, wherein the oxidizing agent is an inorganic peroxide.

11. The method of claim 10, wherein the inorganic peroxide is hydrogen peroxide.

12. The method of claim 8, wherein the second penetration enhancer is selected from the group consisting of mineral oils, alcohols, polyols, fatty alcohols, and fatty acid esters.

13. The method of claim 8, wherein the oxidizing composition includes water, an acrylates polymer, hydrogen peroxide, dimethicone copolyol meadowfoamate, simethicone, phosphoric acid, and a penetrating agent.

14. The method of claim 7, wherein the first penetration enhancer is selected from the group consisting of mineral oils, alcohols, polyols, fatty alcohols, and fatty acid esters.

15. The method of claim 7, wherein the reducing composition is applied to the skin once per day.

16. The method of claim 7, wherein the reducing composition is applied to the skin multiple times per day.

17. The method of claim 7, wherein the reducing composition is applied to the skin once per day for multiple days in sequence.

* * * * *